(12) United States Patent
Grassberger et al.

(10) Patent No.: US 7,514,554 B2
(45) Date of Patent: Apr. 7, 2009

(54) HETEROATOMS-CONTAINING TRICYCLIC COMPOUNDS

(75) Inventors: Maximilian Grassberger, Vienna (AT); Amarylla Horvath, Vienna (AT)

(73) Assignee: Novarits AG, Basel (CH)

( * ) Notice: Subject to any disclaimer, the term of this patent is extended or adjusted under 35 U.S.C. 154(b) by 0 days.

(21) Appl. No.: 11/575,757

(22) PCT Filed: Oct. 10, 2005

(86) PCT No.: PCT/EP2005/010889

§ 371 (c)(1), (2), (4) Date: Apr. 20, 2007

(87) PCT Pub. No.: WO2006/040111

PCT Pub. Date: Apr. 20, 2006

(65) Prior Publication Data

US 2008/0071082 A1    Mar. 20, 2008

(30) Foreign Application Priority Data

Oct. 12, 2004 (GB) ................................. 0422643.7
Dec. 16, 2004 (GB) ................................. 0427599.6

(51) Int. Cl.
*C07D 498/18* (2006.01)

(52) U.S. Cl. ..................................................... 540/456
(58) Field of Classification Search .................. 540/456
See application file for complete search history.

(56) References Cited

U.S. PATENT DOCUMENTS

| 4,464,366 A | 8/1984 | Wehrli et al. ................. 424/246 |
| 6,160,117 A | 12/2000 | Whitton et al. ............. 544/319 |
| 6,667,312 B2 | 12/2003 | Bonk et al. ................. 514/274 |
| 6,706,727 B1 | 3/2004 | Fleissner et al. ............ 514/291 |

FOREIGN PATENT DOCUMENTS

| EP | 0 427 680 | 5/1991 |
| EP | 0 480 623 | 4/1992 |
| EP | 0 626 385 | 10/2003 |

OTHER PUBLICATIONS

C. N. Barry et al., "Cyclodehydration and Chlorination of Simple Diols with Triphenylphosphine and tert-Butyl Hyprochlorite", Journal of Organic Chemistry, vol. 48, No. 17, pp. 2825-2828, (1983).
J.C. Racero et al., "Novel Rearrangement of an Isocaryolane Sequiterpenoid under Mitsunobu Conditions", Journal of Organic Chemistry, vol. 65, No. 23, pp. 7786-7791, (2000).
Luca De L et al., "An efficient route to alkyl chlorides from alcohols using the complex TCT/DMF", Organic Letters, ACS, Waschington, DC, vol. 4, No. 4, pp. 553-555, (2002).

*Primary Examiner*—Bruck Kifle
(74) *Attorney, Agent, or Firm*—Jennifer C. Chapman

(57) ABSTRACT

A process for the production of 33-Epi-33-chloro-FR 520 in one step from FR520 wherein protecting groups are avoided.

7 Claims, No Drawings

HETEROATOMS-CONTAINING TRICYCLIC COMPOUNDS

The present invention relates to heteroatoms-containing tricyclic compounds, e.g. a process for the production of 33-epichloro-33-desoxyascomycin (33-epi-33-chloro-FR 520).

33-Epi-33-chloro-FR 520 is a known compound, e.g. disclosed in EP0427680 (example 66a). 33-Epi-33-chloro-FR 520 of formula

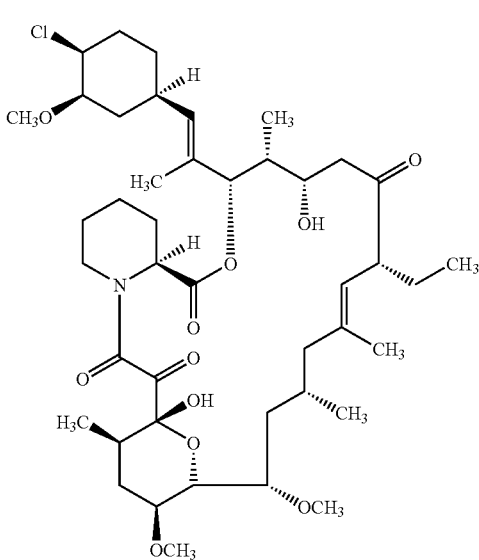

may be useful in immunological-mediated diseases, e.g. useful in the treatment and prevention of inflammatory, autoimmune and hyperproliferative diseases, e.g. including
- skin diseases, such as psoriasis, atopic dermatitis,
- immune-mediated conditions of the eye, such as auto-immune diseases, e.g. including uveitis, keratoplasty and chronic keratitis,
- allergic conditions, e.g. vernal conjunctivitis, inflammatory conditions, corneal transplants.

Processes for the production of 33-Epi-33-chloro-FR 520 are known. We have now found surprisingly a process for the production of 33-Epi-33-chloro-FR 520 from FR520 (ascomycin) in which process the use of protecting groups may be avoided. Such process may be carried out in one single chemical process step.

In one aspect the present invention provides an one-step process for the production of 33-Epi-33-chloro-FR 520 from FR520.

In another aspect the present invention provides a process for the production of 33-epi-33-chloro-FR 520 from FR520 wherein protecting groups are avoided, e.g. wherein protecting group technology is avoided.

In another aspect the present invention provides a process for the production of 33-Epi-33-chloro-FR 520 comprising reacting the compound FR520 with an appropriate chlorinating agent in organic solvent, optionally in the presence of a base, and isolating 33-Epi-33-chloro-FR 520 obtained from the reaction mixture.

In a process according to the present invention FR520, the chlorinating agent and optionally the base, optionally each in organic solvent, or as such, are mixed and the mixture obtained is stirred at appropriate temperature for a period sufficient for reaction. The reaction mixture obtained may be worked up, e.g. analogously to a method as conventional, e.g. by aqueous extraction and evaporation of the organic solvent. The work up residue obtained comprising 33-Epi-33-chloro-FR 520 may be further purified, e.g. by chromatography, crystallization.

An appropriate chlorinating agent includes e.g. dichlorotriphenylphosphorane. The chlorinating agent may be used as such or may be provided in situ, e.g. by treating triphenylphosphine with a chlorinated alkane, e.g. $(C_{1-2})$alkane, such as $CCl_4$, $C_2Cl_6$, preferably $CCl_4$; or by addition of triphenylphosphine to N-chlorosuccinimide in organic solvent.

Organic solvent includes appropriate organic solvent, such as hydrocarbons, e.g. aromatic hydrocarbons, e.g. benzene, toluene; ethers, such as tetrahydrofurane; nitriles, e.g. acetonitrile; chlorinated alkanes, such as $CCl_4$ and mixtures of individual cited solvent. E.g., the reaction mixture may be diluted with a second solvent, e.g., if as the organic solvent toluene is used, preferably with acetonitrile, in order to facilitate stirring. Preferably organic solvent includes toluene, acetonitrile or tetrahydrofurane, or optionally a mixture of toluene and acetonitrile, in case of using triphenylphosphine and N-chlorosuccinimide for the preparation of dichlorotriphenylphosphorane as a chlorinating agent. Preferably organic solvent includes a halogenated alkane in case of using triphenylphosphine and a halogenated alkane for the preparation of dichlorotriphenylphosphorane as a chlorinating agent.

In another aspect the organic solvent in a process of the present invention is selected from the group consisting of aromatic hydrocarbons, ethers and nitriles.

In case of using triphenylphosphine and a chlorinated alkane as a solvent, the chlorinated alkane may be used in one aspect as a halogen source for the production of dichlorotriphenylphosphorane and, in another aspect, as organic solvent, although the addition of further organic solvent, e.g. such as cited above, is not excluded.

Appropriate reaction temperatures include temperatures from room temperature to about 100° C., such as from room temperature to about 80° C., e.g. from room temperature to about 70° C., e.g. from room temperature to 70° C., 80° C. or 100° C. In case of using a chlorinated alkane and triphenylphosphine for the production of the chlorinating agent, such as $CCl_4$, preferably the reaction temperature is reflux temperature of the chlorinated alkane.

E.g. FR520 is treated with dichlorotriphenylphosphorane, e.g. dichlorotriphenylphosphorane is provided by treating triphenylphosphine with
- N-chlorosuccinimide in organic solvent, e.g. organic solvent as described above, preferably an ether or an aromatic hydrocarbon,
- chlorinated alkanes as a chlorinating agent and as a solvent, such as $CCl_4$, in which case no further organic solvent is necessary, although the addition of further organic solvent, e.g. such as described above, is not excluded,
- solid chlorinated alkanes in organic solvent, such as $C_2Cl_6$ in organic solvent, e.g. organic solvent as described above, preferably an ether or an aromatic hydrocarbon, optionally in the presence of a base.

A base includes appropriate bases, such as organic bases, e.g. nitrogen containing bases, preferably such as tert.amines or heterocyclic bases containing at least one nitrogen atom, more preferably aromatic heterocyclic bases, such as a pyridine, an imidazole; preferably a pyridine, such as pyridine, 2,4,6-trimethylpyridine (s-collidine).

In the case of using triphenylphosphine and a chlorinated alkane for the production of a chlorinating agent, during the reaction of FR520 with the chlorinating agent a base optionally may be present. In case of using triphenylphosphine and N-chlorosuccinimide for the production of a chlorinating agent during the reaction of FR520 with the chlorinating agent the presence of a base is preferred, e.g. a base should be present.

In a preferred aspect of the present invention N-chlorosuccinimide is treated with triphenylphosphine in organic solvent and, to the mixture obtained, a base and FR520 are added, e.g. in portions, under stirring and heating.

In another aspect the present invention provides a process for the production of 33-Epi-33-chloro-FR 520, comprising reacting FR 520 in organic solvent with a chlorinating agent in the presence of a base, e.g. under appropriate temperature, wherein the chlorinating agent is provided by treating triphenylphosphine with N-chlorosuccinimide in organic solvent.

In another preferred aspect of the present invention triphenylphosphine is treated with a chlorinated alkane and FR 520 is added under stirring and heating.

In another aspect the present invention provides a process for the production of 33-Epi-33-chloro-FR 520 from FR520, comprising reacting FR 520 with a chlorinating agent in organic solvent, e.g. under appropriate temperature, wherein the chlorinating agent is provided by treating triphenylphosphine with a chlorinated alkane, e.g. wherein the organic solvent preferably is a chlorinated alkane, e.g. in the absence of a base.

The ratio of FR520 and the chlorinating agent should be at least an equivalent ratio, preferably an excess of the chlorinating agent is used, e.g. ascomycin and the chlorinating agent a used in a ratio from about 1:1 to about 1:3 (per equivalent of ascomycin 1 to 3 equivalents of the chlorinating agent), such as from about 1:1 to about 1:2, e.g. from about 1:1 to about 1:5, preferably from about 1:1 to about 1:1.3, e.g. a ratio from 1:1 to 1:3, such as from 1:1 to 1:2, e.g. from 1:1 to 1:5, preferably from 1:1 to 1:1.3 may be appropriate. The ratio of FR520 and the base should be at least an equivalent ratio, preferably an excess of the base is used, e.g. FR520 and the base are used in a ratio from about 1:1 to about 1:10 (per equivalent FR520 1 to 10 equivalents of the base), such as from about 1:2 to about 1:10, e.g. from about 1:3 to about 1:9, preferably from about 1:4 to 1:8;, e.g. a ratio from 1:1 to 1:10, such as from 1:2 to 1:10, e.g. from 1:3 to 1:9, preferably from 1:4 to 1:8 may be appropriate.

After a sufficient period of time which period may be determined by e.g. thin layer chromatography or HPLC, the mixture obtained comprising FR520, the chlorinating agent and optionally a base, is worked up. Work up may be preferably carried out by subjecting to aqueous extraction. From the organic phase obtained by extraction, solvent may be removed, e.g. by distillation, such as evaporation, and the (distillation, evaporation) residue obtained may be subjected to further purification, e.g. subjected to chromatography, e.g. subjected to chromatography over silicagel. 33-Epi-33-chloro-FR 520 is obtained and may be crystallized as appropriate, e.g. from a mixture of water and ethanol.

From chromatography optionally unreacted ascomycin may be recollected. Recollected ascomycin may again undergo a reaction according to the present invention.

FR520 is a compound of formula

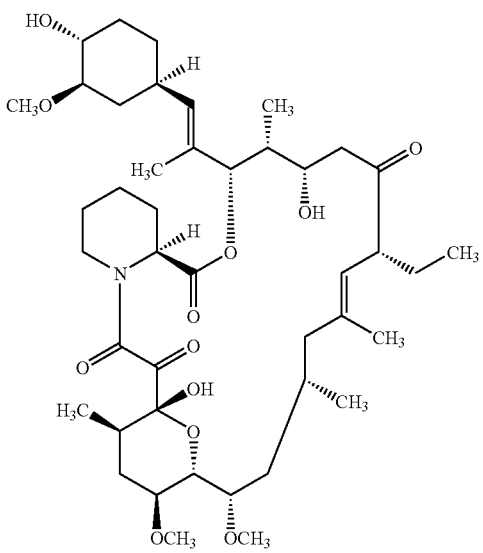

ASC

In the following examples all temperatures are in degree centigrade and are uncorrected.

The following abbreviations are used:
FR520 ascomycin, compound of formula ASC
33-epi-33-chloro-FR 520 33-epichloro-33-desoxyascomycin (pimecrolimus), compound of formula I

EXAMPLE 1

33-Epi-33-chloro-FR 520

9.69 g of s-collidine (2,4,6-trimethylpyridine) and 15.84 g of FR520 are added to a solution of 24.8 mMol of dichlorotriphenylphosphine in 160 ml of toluene. The mixture obtained is stirred at 60° for 1 hour, $H_2O$ is added, two phases obtained are separated and the organic layer obtained is washed with aqueous, saturated NaCl solution and dried. From the mixture obtained solvent is evaporated and the evaporation residue obtained is subjected to chromatography over silicagel. 33-epi-33-chloro-FR 520 is obtained. Yield: 51.4%. From chromatography a fraction containing unreacted FR520 is obtained. The fraction containing unreacted FR520 is triturated with diethylether and 4.5 g of crude ascomycin are obtained which may undergo a reaction as described in example 1 above or in any of the examples 2 or 3 below.

Analogously as described in example 1 but using FR520, dichlorotriphenylphosphine and organic solvent and bases as set out in TABLE 1 below, in amounts and ratios as set out in TABLE 1 below, 33-epi-33-chloro-FR 520 is obtained in yields (%) as set out in TABLE 1 below.

TABLE 1

| EX | FR520 (g) | RATIO FR520:CL-A:BASE | Base | Solvent | Yield (%) |
| --- | --- | --- | --- | --- | --- |
| 1a | 0.2 | 1:1.25:4 | pyridine | toluene | 55.4 |
| 1b | 2.0 | 1:1:4 | pyridine | toluene | 58.6 |
| 1c | 2.0 | 1:1:8 | pyridine | toluene | 40.7 |
| 1d | 2.0 | 1:1.25:5.5 | imidazole | acetonitrile | 13.6 |
| 1e | 2.0 | 1:1.25:5.5 | pyridine | acetonitrile | 32.4 |

TABLE 1-continued

| EX | FR520 (g) | RATIO FR520:CL-A:BASE | Base | Solvent | Yield (%) |
|---|---|---|---|---|---|
| 1f | 2.0 | 1:1.2:4 | s-collidine | toluene | 60.0 |
| 1g | 10 | 1:1.2:4 | pyridine | toluene | 52.4 |
| 1h | 48 | 1:1.1:4 | pyridine | toluene | 48.8 |
| 1i | 27*) | 1:1.2:4 | s-collidine | toluene | 33.8 |

*)Ascomycin unreacted and recovered from other examples

In TABLE 1 above FR520 (g) means the amount of FR520 in gram, "RATIO FR520:CL-A:BASE" means the molar ratio of FR520:dichlorotriphenylphosphine:base; and "EX" means the Example number.

EXAMPLE 2

33-Epi-33-chloro-FR 520

A solution of 277 mg of FR520 and 138 ml of triphenylphosphine in 8 ml of CCl$_4$ is heated to reflux for 18 hours. To the mixture obtained toluene is added, the mixture obtained is filtrated and from the filtrate obtained solvent is evaporated. The evaporation residue is subjected to chromatography over silicagel. 33-Epi-33-chloro-FR 520 is obtained. Yield: 45%.

EXAMPLE 3

33-Epi-33-chloro-FR 520

A solution of 100 mg triphenylphosphine in 1 ml of tetrahydrofurane (THF) is added dropwise to 50 mg of N-chlorosuccinimide in 1.2 ml of THF. The mixture obtained is stirred for 0.5 hours at room temperature and 0.1 ml pyridine followed by a solution of 244 mg of FR520 in 2 ml of THF are added and the mixture obtained is stirred for 1 hour at 65°. The mixture is diluted with toluene, water is added, and the two phases obtained are separated. The organic layer obtained is washed with 1N HCl, H$_2$O and saturated NaCl solution and dried. From the solution obtained solvent is evaporated and the evaporation residue obtained is subjected to chromatography over silicagel. 33-Epi-33-chloro-FR 520 is obtained. Yield: 48.1%.

EXAMPLE 4

Crystallization of 33-Epi-33-chloro-FR 520

27 g of crude 33-epi-33-chloro-FR 520, obtained according to a method as described in any of the examples 1 to 3, are dissolved in 180 ml of ethanol and 65 ml water are added. The mixture obtained is kept at 4°, further water is added and the mixture obtained is kept for further 4 hours at 4°. 23.5 g of crystallized 33-epi-33-chloro-FR 520 are obtained in a purity of 98%.

What is claimed is:

1. A one-step process for the production of a compound of formula I

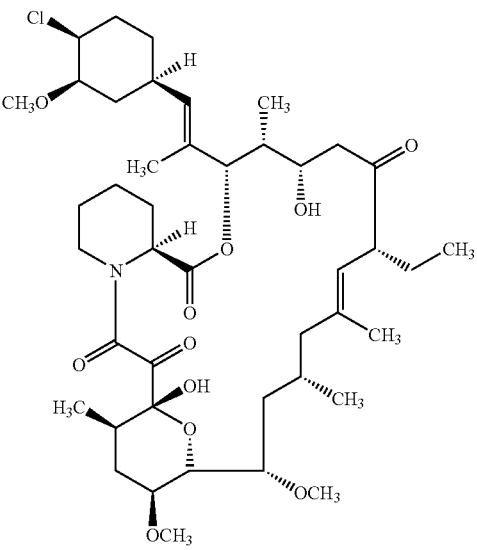

from a compound of formula ASC

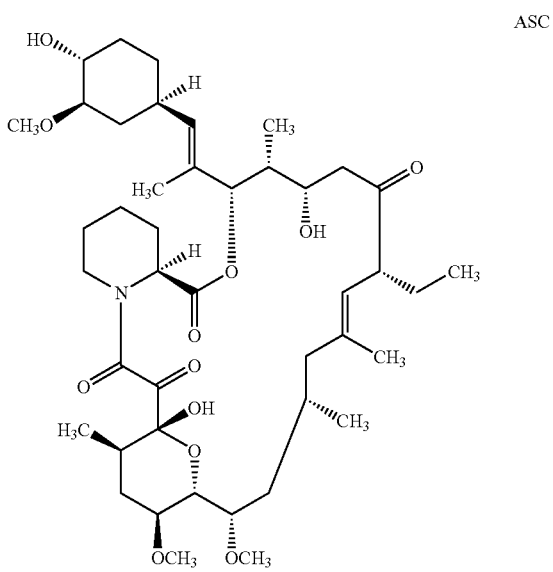

said process comprising reacting the compound of formula ASC with an appropriate chlorinating agent in organic solvent, in the presence of a base, and isolating a compound of formula I obtained from the reaction mixture, wherein said process does not use protecting groups.

2. A process according to claim 1, wherein the chlorinating agent is dichlorotriphenylphosphorane.

3. A process according to claim 1 comprising reacting FR 520 in organic solvent with a chlorinating agent in the presence of a base, wherein the chlorinating agent is provided by treating triphenylphosphine with N-chlorosuccinimide in organic solvent.

4. A process according to claim 3, wherein the organic solvent is selected from the group consisting of aromatic hydrocarbons, ethers and nitriles.

5. A process according to claim 1 wherein the base is a pyridine.

6. A process according to claim 1 comprising reacting a compound of formula ASC with a chlorinating agent in organic solvent, wherein the chlorinating agent is provided by treating triphenylphosphine with a chlorinated alkane.

7. A process according to claim 6, wherein a chlorinated alkane is CCl4.

* * * * *